United States Patent
Klein et al.

(10) Patent No.: US 12,025,427 B2
(45) Date of Patent: Jul. 2, 2024

(54) OPTICAL MEASURING METHOD AND OPTICAL MEASURING APPARATUS

(71) Applicant: DENTSPLY SIRONA INC., York, PA (US)

(72) Inventors: Konrad Klein, Heidelberg (DE); Peter Fritz, Mannheim (DE); Anders Adamson, Darmstadt (DE)

(73) Assignee: DENTSPLY SIRONA INC., York, PA (US)

( * ) Notice: Subject to any disclaimer, the term of this patent is extended or adjusted under 35 U.S.C. 154(b) by 635 days.

(21) Appl. No.: 17/258,812

(22) PCT Filed: Jun. 14, 2019

(86) PCT No.: PCT/EP2019/065650
§ 371 (c)(1),
(2) Date: Jan. 8, 2021

(87) PCT Pub. No.: WO2020/011483
PCT Pub. Date: Jan. 16, 2020

(65) Prior Publication Data
US 2021/0267461 A1 Sep. 2, 2021

(30) Foreign Application Priority Data
Jul. 10, 2018 (DE) ...................... 10 2018 211 371.8

(51) Int. Cl.
*A61B 5/00* (2006.01)
*G01B 11/24* (2006.01)
(Continued)

(52) U.S. Cl.
CPC ............ *G01B 11/24* (2013.01); *A61B 5/0088* (2013.01); *G06T 7/514* (2017.01); *G06T 7/55* (2017.01);
(Continued)

(58) Field of Classification Search
CPC .......... G01B 11/24; G06T 7/514; G06T 7/55; G06T 2207/10024; G06T 2207/30036; A61B 5/0088
See application file for complete search history.

(56) References Cited

U.S. PATENT DOCUMENTS

2010/0303341 A1* 12/2010 Hausler ................ A61B 5/1079
382/154
2014/0272765 A1* 9/2014 Andreiko ........... A61B 1/00006
433/29

FOREIGN PATENT DOCUMENTS

DE 102014207667 A1 10/2015
EP 2172799 A1 4/2010
(Continued)

OTHER PUBLICATIONS

Besl et al.; "A Method for Registration of 3-D Shapes" IEEE Transactions on pattern analysis and machine Intelligence; vol. 14, No. 2; 1992.
(Continued)

*Primary Examiner* — David F Dunphy
(74) *Attorney, Agent, or Firm* — DENTSPLY SIRONA INC.

(57) ABSTRACT

The invention relates to an optical measuring method for the three-dimensional detection of the surface of an object using an optical recording unit. The optical recording unit is moved relative to the object during a first measurement time interval, height maps are successively detected by the recording unit at a recording frequency, and at least some of the detected height maps are each added to an overall height map and displayed. The recording frequency is regulated by control signals during the measurement time interval. The control signals are generated spaced apart in time and for the purposes of producing each control signal, a statistic for the quality of the height map is determined for the respectively (Continued)

last detected height image and used for producing the control signal. The statistic is the overall intensity and/or the maximum intensity and/or the contrast and/or the number of extracted data points and/or a quality of extracted data points and/or the signal-to-noise ratio and/or the contrast of an additionally generated color image.

8 Claims, 1 Drawing Sheet

(51) Int. Cl.
G06T 7/514 (2017.01)
G06T 7/55 (2017.01)

(52) U.S. Cl.
CPC ............... *G06T 2207/10024* (2013.01); *G06T 2207/30036* (2013.01)

(56) References Cited

FOREIGN PATENT DOCUMENTS

| WO | 2015036467 A1 | 3/2015 |
| WO | 2017062044 A1 | 4/2017 |

OTHER PUBLICATIONS

Pulli et al.; "Multiview Registration of Large Data Sets"; Proceedings, Second International Conference on 3D Digital Imaging and Modeling, Ottawa 1999; pp. 160-168.
Lorensen et al; "Marching Cubes: A High Resolution 3D Surface Construction Algorithm"; ACM SIGGRAPH Computer Graphics; vol. 21, No. 4; Aug. 1987; pp. 163-169.
International Search Report; PCT/EP2019/065650; Aug. 23, 2019 (completed); Sep. 4, 2019 (mailed).
International Preliminary Report on Patentability; PCT/EP2019/065650; Aug. 23, 2019 (completed); Sep. 4, 2019 (mailed).
Written Opinion of the International Search Authority; PCT/EP2019/065650; Aug. 23, 2019 (completed); Sep. 4, 2019 (mailed).

\* cited by examiner

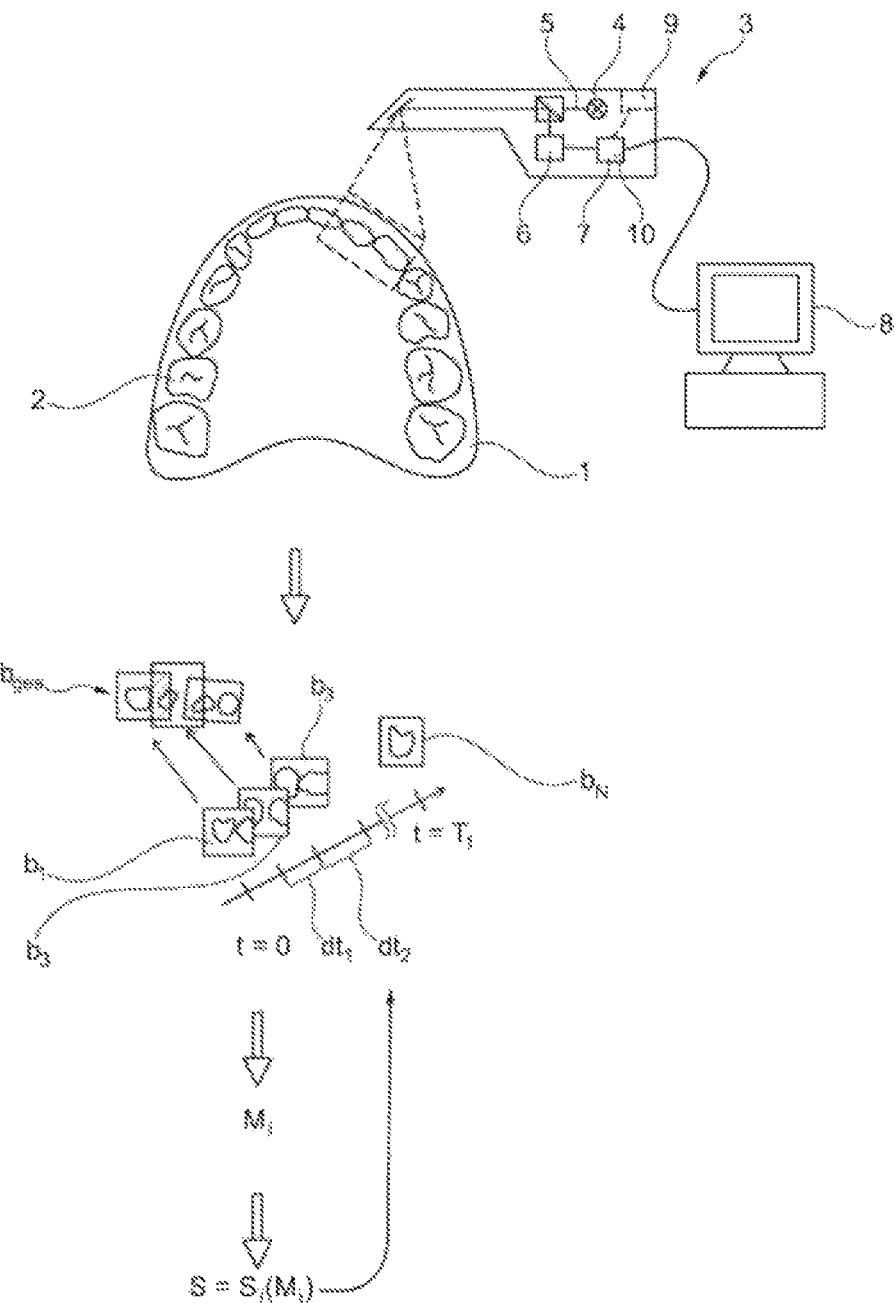

ized optical measuring apparatuses # OPTICAL MEASURING METHOD AND OPTICAL MEASURING APPARATUS

CROSS-REFERENCE TO RELATED APPLICATIONS

This is a National Phase application of International Application No. PCT/EP2019/065650, filed Jun. 14, 2019, which claims the benefit of and priority to German Application Ser. No. 102018211371.8, filed on Jul. 10, 2018, which are herein incorporated by reference for all purposes.

TECHNICAL FIELD

The invention relates to an optical measuring method for the three-dimensional detection of the surface of an object using an optical recording unit, wherein the optical recording unit is moved relative to the object during a first measurement time interval, height maps are successively detected by the recording unit at a recording frequency, wherein the detected height maps are already added to an overall height map during the measurement time interval and the overall height map is displayed.

BACKGROUND OF THE INVENTION

EP 2 172 799 A1 discloses an optical measuring apparatus that allows a three-dimensional optical detection of an object by means of a confocal imaging system. The optical measuring apparatus known from WO 2015/036467 also works confocally and additionally with a moving pattern projected onto the object.

In order to measure objects whose size exceeds the size of the recording region of the measuring apparatus, several individual images are generated and assembled into an overall image. The individual images are generated successively, while the measuring apparatus and the object are moved relative to one another. The relative orientations of the individual images relative to one another must be determined for the assembly of the individual images. This step is referred to as registration. Algorithms for registering image data are known, for example, from "A Method for Registration of 3-D Shapes" by Besl et al., IEEE Transactions on pattern analysis and machine intelligence, vol. 14, no. 2, 1992, or from "Multiview Registration of Large Data Sets" by Pulli, Proceedings, Second International Conference on 3D Digital Imaging and Modeling, Ottawa 1999, pp. 160-168.

Both the generation of projection patterns or of light for illuminating the object in general and the registration and transmission of the individual data sets requires energy, wherein the waste heat resulting from the energy consumption is undesirable in particular for measuring apparatuses to be used intraorally, e.g., intraoral cameras.

One way to reduce heat generation or prevent unnecessary heat generation is to avoid the generation of unnecessary image data sets, i.e., image data sets not required for the overall image.

In order to prevent unnecessary images, it is known, for example, to direct the user through feedback during the recording time interval. For example, DE 10 2014 207 667 A1 discloses displaying to the user already detected regions of the object in a standard model during the recording. The user can react accordingly and not measure the already sufficiently measured regions again.

In light of this background, the object of the present application is to improve the known measuring apparatuses and measuring methods and in particular to reduce the energy consumption and computing effort in a reliable manner and, if possible, independently of the user and the capabilities of the user.

SUMMARY OF THE INVENTION

The object is achieved by an optical measuring method according to Claim 1 and an optical measurement system according to Claim 8. Advantageous developments are listed in the dependent claims.

One subject matter of the invention is an optical measuring method for the three-dimensional detection of the surface of an object using an optical recording unit and an optical measurement system designed for carrying out the optical measuring method, with an optical recording unit, a computer-readable storage unit, a computing unit, and a display unit.

During a first measurement time interval, the optical recording unit is moved relative to the object, wherein height maps are successively detected by the recording unit at a recording frequency. At least a portion of the detected height maps is added to an overall height map and displayed during the measurement time interval.

The recording frequency is regulated by control signals during the measurement time interval and the control signals are generated at time intervals during the measurement time interval. For generating each control signal for the respectively last detected height map, at least one statistic for the quality of the height map is determined and used for generating the control signal, wherein the statistic is the overall intensity and/or the maximum intensity and/or the contrast and/or the number of extracted data points and/or a quality of extracted data points and/or the signal-to-noise ratio and/or the contrast of an additional color image generated, for example, by means of a color image camera.

It goes without saying that each statistic for the quality. e.g., the overall intensity, is taken alone as a basis for the control signal or the control signal is alternatively generated taking into account any selection of the aforementioned quality statistics, e.g., the overall intensity and the maximum intensity, or also taking into account all the aforementioned statistics.

All pixels or image points detected by the recording unit and used for a height map are referred to as extracted data points.

Referred to as a height map is a pixel matrix or image matrix in which each pixel or image point contains three-dimensional information, namely the three-dimensional position of the object surface or the height of the object surface for the respective image point in the recording region. The three-dimensional information was extracted, for example, from an image sequence, e.g., by means of phase shift triangulation. The overall height map is composed of the many height maps recorded during the measurement time interval so that objects can also be measured whose size exceeds the size of the recording region of the recording unit.

The detected height maps or the overall height map assembled from the height maps can be represented in different ways. It is advantageous, for example, to identify or represent an object surface within the volume data set as a triangulated network. For example, the surface can be represented according to the method described in "Marching Cubes: A High Resolution 3D Surface Construction Algorithm," W. E. Lorensen and H. E. Cline, ACM SIGGRAPH Computer Graphics, vol. 21, no. 4, pp. 163-169, August 1987.

A time span between switching on the optical recording unit and switching off the optical recording unit is referred to as first measurement time interval.

It goes without saying that the recording frequency can basically take on any values. Accordingly, during the measurement time interval, there may be regular dead times during which the recording frequency is zero.

In order to save energy and/or computing effort, it is advantageous to keep the recording frequency as low as possible. On the other hand, a certain recording frequency is necessary to detect a recording region and to obtain a certain quality of the overall height map. The transmission of recording data from the recording unit to a computing unit can also be temporarily suspended to save energy.

By determining the quality of the detected data during the measurement, it is possible to adjust the recording frequency promptly, in particular still during the measurement time interval, to the current state and thereby ensure sufficient quality on the one hand and, on the other hand, minimum energy consumption and/or computing effort.

An assessment of the quality of the respectively last recorded image and thus an estimation of the quality of the image data currently recorded during the application is possible based on the one or more quality statistics extracted from the last height map or determined for the height map.

A high overall intensity, a high maximum intensity, a high contrast, a large number of extracted data points, a high quality of the extracted data points, a high signal-to-noise ratio, and a high contrast of an additionally generated color image are each indications of a high quality of the detected image data. The variables mentioned can thus be used individually or several or all of the variables mentioned can also be used to assess the quality of the detected image data objectively and independently of a user. For example, the respectively determined statistics are compared to a corresponding limit value for this purpose.

If the quality of the detected image data, i.e., of the individual height maps, is high, a few height maps are already sufficient to generate an overall height map of good quality. If, on the other hand, the quality of the individual height maps is poor, the same quality of the overall height map is only achieved if a significantly larger number of height maps is used to generate it.

It goes without saying that each of the mentioned statistics is used solely to assess the quality of the image data and that an even more comprehensive and/or more reliable estimate of the quality is possible by using several or all of the mentioned statistics.

The recording frequency and/or illumination intensity is adapted according to the invention to the determined state, i.e., the quality of the detected image data.

For generating the control signals, a computing unit is provided, for example, which communicates with the optical recording unit via a cable or wirelessly. Alternatively, a computing unit can be integrated in the optical recording unit.

The control signals are generated at fixed time intervals, i.e., at a fixed frequency. Alternatively, the control signals are generated at different time intervals, e.g., due to a trigger signal. According to another alternative embodiment, an at least temporally associated control signal is generated for each detected height map so that the time interval for the control signal generation is based on the recording frequency of the height maps.

Regulating the recording frequency as a function of a current state of the image makes it possible to reduce the energy consumption in case of good quality of the data.

The advantage of the method according to the invention and of the apparatus according to the invention is therefore reduced energy consumption, whereby in particular heating of the recording unit is also reduced. At the same time, it is ensured that the quality of the images or the overall height map is not reduced.

During the first measurement time interval, the object is advantageously illuminated by the recording unit using an illumination beam with a light intensity and the light intensity is regulated by means of the control signal during the measurement time interval. By regulating the light intensity depending on the current state of the recording unit, the light intensity can be reduced whenever possible, wherein sufficient quality of the data is ensured.

At least one sensor signal from at least one sensor is advantageously used to generate each control signal. The temperature can be monitored by means of a temperature sensor, for example. Alternatively or supplementally, it can be determined by means of a motion sensor, for example, whether the optical recording unit is in a resting position (no movement), is positioned for an image (relatively rapid movement of the [sic] from a resting position to the object to be recorded), or the object is being measured (slow movement) in order to adjust the recording frequency accordingly.

Advantageously, prior to adding a height map to the overall height map, a registration method is selected for the addition as a function of the recording frequency.

The optical measurement system according to the invention comprises an optical recording unit, a computer-readable storage unit, a computing unit, and a display unit and is designed to carry out the optical measuring method described above.

BRIEF DESCRIPTION OF THE DRAWINGS

Exemplary embodiments of the invention are shown in the drawing. The following is shown:

FIG. 1 a schematic representation of a first embodiment of a recording method according to the invention.

DETAILED DESCRIPTION OF THE INVENTION

FIG. 1 schematically illustrates a first embodiment of a recording method according to the invention.

According to the exemplary embodiment, a lower jaw 1 with teeth 2 is measured as an object by means of an optical recording unit 3. The optical recording unit 3 is designed as an intraoral camera and comprises a light source 4 and a light detector 6 and is connected to a computing unit 7 with a display means 8.

The measurement is carried out during a time interval TI, wherein the intraoral camera 3 is moved over the teeth 2 of the lower jaw 1 and/or empty spaces in the lower jaw 1. The light source 4 provides an illumination beam 5 and the light detector 6 detects reflected light.

The reflected light is detected at a recording frequency $f_A$, wherein a data set is respectively detected by the light detector 6 and transmitted to the computing unit at a time interval $dt=1/f_A$. For each data set, the computing unit respectively calculates a height map $b_i$, i=1 ... N and stores the latter in a storage medium of the computing unit 8. The recording frequency $f_A$ can be changed so that the time intervals $dt_i$ between consecutively recorded height maps $b_i$, $b_{i+1}$ are not necessarily identical.

The height maps b± generated are already gradually assembled during the measurement time interval TI to form an overall height map $b_{ges}$ wherein the overall height map $b_{ges}$ is already displayed by means of the display means 8 during the formation. It goes without saying that, where applicable, not all generated height maps $b_i$ are used for the overall height map, but that individual height maps bi are sorted out due to lack of quality, for example.

First, a first height map $b_1$ is stored and displayed as an overall height map $b_{ges}$. Further recorded height maps $b_i$, i=2 . . . N are then continuously added to the overall height map bges and the new overall height map bges is displayed in new form after adding each further height map. A relative orientation of the height map bi relative to the overall height map $b_{ges}$ is determined, for example, based on an overlap (shown in a hatched fashion) of the height map bi with the overall height map $b_{ges}$, i.e., the height maps $b_i$ recorded up to now, in particular the height map $b_{i-1}$ recorded immediately before.

In addition, in the exemplary embodiment shown, at least one statistic M of the quality of the height map $b_i$ is determined for each height map bi, and the recording frequency $f_A$ is regulated based on the determined quality.

The quality statistic $M_i$ is the overall intensity and/or the maximum intensity and/or the contrast and/or the number of extracted data points and/or a quality of extracted data points and/or the signal-to-noise ratio and/or the contrast of an additionally generated color image.

Based on the first statistic $M_i$, a first control signal $S=S_i(M_i)$ for controlling the recording frequency $f_A$ is generated. The recording frequency $f_A$ of the light detector 6 is then regulated. i.e., changed where applicable, by means of the control signal S by means of a control unit 10, which is part of the optical recording unit 3 in the illustrated exemplary embodiment. The next height map $b_{i+1}$ is detected accordingly at a time interval $dt_{i+1}=1/f_A$, wherein $f_A$ refers to the regulated recording frequency.

In an alternative embodiment, a sensor signal of a sensor 9 (shown dashed) is supplementally used to calculate the control signal S. For example, the movement of the intraoral camera 3 is tracked by means of an integrated inertial measurement system, wherein the alignment of the individual height maps $b_i$ relative to one another can be deduced from the movement of the camera 4.

LIST OF REFERENCE SIGNS

1 Object
2 Tooth
3 Recording unit
4 Light source
5 Illumination beam
6 Light detector
7 Computing unit
8 Display unit
9 Sensor
10 Control unit
$b_{ges}$ Overall height map
$b_i$ Height maps
$f_A$ Recording frequency
dt Time interval
$M_i$ Statistic for the quality of the height map $b_i$
S Control signal
T1 Recording time interval

The invention claimed is:

1. Optical measuring method for the three-dimensional detection of the surface of an object using an optical recording unit, comprising:
   moving the optical recording unit relative to the object during a first measurement time interval,
   successively detecting, by the recoding unit, height maps, at a recording frequency during the first measurement time interval,
   adding at least a portion of the detected height maps to an overall height map during the measurement time interval and displaying the overall height map
   wherein the recording frequency is regulated during the measurement time interval by means of control signals,
   wherein the control signals are generated at time intervals during the measurement time interval,
   wherein for generating a control signal for a height map, a measure for the quality of the height map is determined and used for generating the control signal,
   wherein the measure is the overall intensity and/or the maximum intensity and/or the contrast and/or the number of extracted data points and/or a quality of extracted data points and/or the signal-to-noise ratio and/or the contrast of an additionally generated color image,
   wherein by determining the quality of the height map during the first measurement time interval, the recording frequency is adjusted such both that a predetermined quality of the height map and a lowest possible recording frequency is ensured, wherein the quality of the overall height map is determined on the basis of one or more quality measures determined for the height map.

2. Optical measuring method according to claim 1 wherein the additionally generated color image is generated by means of a color image camera.

3. Optical measuring method according to claim 1, wherein during the first measurement time interval, the object is illuminated by the recording unit using an illumination beam with a light intensity and the light intensity is regulated by means of the control signal during the measurement time interval.

4. Optical measuring method according to claim 1, wherein at least one sensor signal by at least one sensor is additionally used for generating each control signal.

5. Optical measuring method according to claim 1, wherein the time intervals between the generation of control signals during the measurement time interval are predetermined by a predetermined frequency.

6. Optical measuring method according to claim 1, wherein a control signal is determined for each detected height map, wherein the time intervals between the generation of control signals during the measurement time interval are predetermined by the recording frequency.

7. Optical measuring method according to claim 1, wherein, before adding the height map to the overall height map, a registration method for the addition is selected as a function of the recording frequency.

8. Optical measurement system, comprising an optical recording unit, a computer-readable storage unit, a computing unit, and a display unit, wherein the optical measurement system is designed to carry out the optical measuring method according to claim 1.

* * * * *